(12) United States Patent
Ahn et al.

(10) Patent No.: US 9,170,216 B2
(45) Date of Patent: Oct. 27, 2015

(54) PINHOLE DETECTION SYSTEM OF FUEL CELL

(71) Applicants: Hyundai Motor Company, Seoul (KR); Kia Motors Corporation, Seoul (KR)

(72) Inventors: Sang Yeoul Ahn, Seoul (KR); Keun Je Lee, Gyunggi-do (KR); Sang Hyun Cho, Seoul (KR); Jea Suk Park, Gyunggi-do (KR); Sung Keun Lee, Gyunggi-do (KR); Byung Ki Ahn, Gyunggi-do (KR); Tae Won Lim, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 14/150,116

(22) Filed: Jan. 8, 2014

(65) Prior Publication Data

US 2014/0119499 A1    May 1, 2014

(30) Foreign Application Priority Data

Nov. 26, 2009  (KR) .................. 10-2009-0115265

(51) Int. Cl.
*G01N 23/04* (2006.01)
*H01M 8/04* (2006.01)

(52) U.S. Cl.
CPC ........ *G01N 23/046* (2013.01); *G01N 2223/419* (2013.01); *H01M 8/04671* (2013.01)

(58) Field of Classification Search
CPC ................ G01N 23/046; G01N 2223/419
USPC .................... 378/10, 20, 53, 84, 85, 161
See application file for complete search history.

(56) References Cited

U.S. PATENT DOCUMENTS 4,872,191 A * 10/1989 Bernardi ................. 378/150
4,989,225 A    1/1991 Gupta et al.
(Continued)

FOREIGN PATENT DOCUMENTS

JP    2008-282644 A    11/2008
JP    2009-210371 A    9/2009

OTHER PUBLICATIONS

S. H. Lau et al., "Non Invasive, Multi-length Scale Characterization of Smart Materials, Membranes, Sensors with a novel high resolution and high contrast CT," ICMAT 2007.*
(Continued)

*Primary Examiner* — Allen C. Ho
(74) *Attorney, Agent, or Firm* — Mintz Levin Cohn Ferris Glovsky and Popeo, P.C.; Peter F. Corless

(57) ABSTRACT

A pinhole detection system of a fuel cell element unit including a density measurement module that calculates a density of a fuel cell element unit using weight and volume data measured from electronic weight balance and 3D scan type volume integrator. Photon energy ranges of X-ray beam and window species of the pinhole detection system automatically are selected from Group 1 or Group 2 according to the density reference point for a fuel cell element, and a stage on which a fuel cell element unit is disposed to be detected. A drive portion that moves the stage to rotate the fuel cell element unit. An X-ray source is disposed at one side of the stage to apply X-ray to the fuel cell element unit that rotates. An image detector detects an X-ray penetrating the fuel cell element unit, and a computer tomography that reconstructs a three dimensional tomogram.

6 Claims, 5 Drawing Sheets

(56) References Cited

U.S. PATENT DOCUMENTS

| | | | |
|---|---|---|---|
| 5,012,498 A | 4/1991 | Cuzin et al. | |
| 5,023,895 A | 6/1991 | McCroskey et al. | |
| 5,119,408 A | 6/1992 | Little et al. | |
| 5,717,732 A * | 2/1998 | Tam | 378/4 |
| 5,866,907 A * | 2/1999 | Drukier et al. | |
| 6,041,132 A | 3/2000 | Isaacs et al. | |
| 6,047,041 A | 4/2000 | Ellinger | |
| 6,104,776 A | 8/2000 | Oikawa | |
| 6,377,659 B1 | 4/2002 | Snyder et al. | |
| 6,389,101 B1 | 5/2002 | Levine et al. | |
| 6,408,052 B1 | 6/2002 | McGeoch | |
| 6,459,760 B1 * | 10/2002 | D'Ambrosio | 378/43 |
| 6,553,094 B1 | 4/2003 | Bernardi et al. | |
| 6,748,045 B2 | 6/2004 | West et al. | |
| 6,807,248 B2 | 10/2004 | Mihara et al. | |
| 7,082,182 B2 * | 7/2006 | Zhou et al. | 378/10 |
| 7,110,489 B2 * | 9/2006 | Roy et al. | 378/20 |
| 7,130,375 B1 | 10/2006 | Yun et al. | |
| 7,177,388 B2 | 2/2007 | Takagi et al. | |
| 7,215,736 B1 | 5/2007 | Wang et al. | |
| 7,254,211 B2 | 8/2007 | Hunt et al. | |
| 7,286,630 B2 | 10/2007 | Holt | |
| 7,286,640 B2 | 10/2007 | Yun et al. | |
| 7,352,840 B1 | 4/2008 | Nagarkar et al. | |
| 7,356,115 B2 | 4/2008 | Ford et al. | |
| 7,492,862 B2 | 2/2009 | Bendahan | |
| 7,499,521 B2 | 3/2009 | Wang et al. | |
| 7,539,283 B2 | 5/2009 | Bendahan | |
| 7,551,714 B2 * | 6/2009 | Rothschild | |
| 7,775,715 B2 | 8/2010 | Warner et al. | |
| 7,792,242 B2 | 9/2010 | Kamegawa | |
| 7,813,470 B2 | 10/2010 | Kuwabara | |
| 7,844,027 B2 | 11/2010 | Harding et al. | |
| 8,422,626 B2 * | 4/2013 | Jin et al. | 378/10 |
| 8,777,485 B2 * | 7/2014 | Holt | 378/207 |
| 2011/0122991 A1 * | 5/2011 | Ahn et al. | |

OTHER PUBLICATIONS

M. Feser, "Sub-micron resolution CT for failure analysis and process development," Meas. Sci. Technol. 19, 2008.*

Andrei Tkachuk et al., "High-resolution x-ray tomography using laboratory sources", Proc. of SPIE, vol. 6318, 63181D, (2006).

H. Lau et al., "Non Destructive Failure Analysis Technique With a Laboratory Based 3D X-ray Nanotomography System," LSI Testing Symposium 2006, Osaka, Japan.

* cited by examiner

PINHOLE DETECTION SYSTEM OF FUEL CELL

CROSS-REFERENCE TO RELATED APPLICATION

The present application is a continuation in part of U.S. application Ser. No. 14/100,900, filed on Dec. 9, 2013, which is a continuation in part of U.S. application Ser. No. 12/815,320, filed on Jun. 14, 2010, which claims under 35 U.S.C. §119(a) priority to and the benefit of Korean Patent Application No. 10-2009-0115265 filed in the Korean Intellectual Property Office on Nov. 26, 2009. Each of the aforementioned patent applications are hereby incorporated by reference in their entirety.

BACKGROUND OF THE INVENTION (a) Field of the Invention

The present invention relates to a pinhole detection system of a fuel cell. More particularly, the present invention relates to a pinhole detection system of a fuel cell that detects a pinhole formed inside a fuel cell stack element, especially MEAs and bipolar plates.

(b) Description of the Related Art

Generally, a fuel cell system generates electrical energy from chemical energy.

A fuel cell system includes a fuel cell stack that generates electrical energy, a fuel supply system supplying fuel (hydrogen) with the fuel cell stack, an air supply system supplying oxygen of air, which is an oxidizing agent that is necessary for electrochemical reaction of the fuel cell stack, and a heat and water management system that controls the operating temperature and the moisture of the fuel cell stack.

Preferably, the fuel cell stack is made by stacking three layers of membrane-electrode assembly (MEA), two gas diffusion layers (GDL), and a bipolar plate, alternately.

However, MEA and bipolar plate of a pinhole can be formed during making process for fabricating the MEA and pressing process for fabricating the bipolar plate in each. Further, as the MEA and the GDL are joined (or hot pressed) to improve productivity, a pinhole can be formed through an electrolyte membrane of the MEA by carbon fiber of the GDL.

The pinhole of the MEA and the bipolar plate generates a burning phenomenon by the chemical reaction of oxygen and hydrogen to meet each other directly and pollution phenomenon of the MEA by leakage of antifreeze, such that output performance of the fuel cell stack and durability are decreased and the fuel cell stack can be shut down.

Accordingly, there is a need in the art to inspect the fuel cell stack for a pinhole to improve the quality of the fuel cell stack. Further, there remains a need in the art to inspect a pinhole, which is formed inside the stack element.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention provides a pinhole detection system for a fuel cell element unit having that preferably effectively detects a pinhole that is formed within a fuel cell element unit.

A pinhole detection system of a fuel cell element unit may include a density detection module that detects a density of a fuel cell element unit, a stage on which a fuel cell element unit is disposed to be detected, a drive portion that is configured to move the stage so as to rotate the fuel cell element unit, an X-ray source that is disposed at one side of the stage to apply X-ray to the fuel cell element unit that rotates, an image detector that detects an X-ray penetrating the fuel cell element unit, a computer tomography that reconstructs a three dimensional tomogram wherein a plurality of projections that are detected by the image detector are used to form a three dimensional tomogram, and a determiner that selects the photon energy level of x-ray and a X-ray window according to a density level of a fuel cell element unit, wherein a focus of the X-ray source ranges from 0.1 to 10 μm, a capacity thereof ranges from 2 to 160 keV, a target thereof includes Rh, Cr, Cu, or W, and the X-ray window is made of one of beryllium, boron family, silicon, nitride family, or polymer family, a resolution of image detector is lower than 1 μm, a magnification thereof ranges from 2000 to 15000, and a vacuum rate inside a discharge pipe of the X-ray source is below $10^{-7}$ torr.

The density of the fuel cell element unit may be calculated by values that are measured by an electronic weight balance and a 3D scan type volume integrator.

The pinhole detection system may further include a group 1 and a group 2 modules with different systems of photon energy level and window group based on a reference point 2.0 g/cm$^3$ that is a density of a fuel cell element unit.

If the density value of fuel cell element unit is lower than or equal to a predetermined density value of the 2.0 g/cm$^3$, the pinhole detection system selects a group 1 in which a X-ray photon energy levels is less than or equal to 60 keV such as 5~60 keV and the X-ray window is made of beryllium, and if the density of the fuel cell element unit is larger than a predetermined density value of the 2.0 g/cm$^3$, the pinhole detection system selects a group 2 in which a X-ray photon energy levels is range of 61~160 keV and the X-ray window is made of one of boron family, silicon, nitride family, or polymer family.

The pinhole detection system may further includes a condense lens that is disposed between the X-ray source and the fuel cell element unit, through which X-ray penetrates.

The pinhole detection system may further includes a filter that is disposed between the X-ray source and the fuel cell element unit, through which X-ray penetrates.

The pinhole detection system may further includes a zone plate that is disposed between the X-ray source and the fuel cell element unit, through which X-ray penetrates.

As described herein, in a pinhole detection system of a fuel cell element unit according to the present invention, the fuel cell element unit is suitably rotated on the stage, X-ray is applied to the rotating unit to gain the tomogram thereof, and the tomogram is suitably reconstructed to be a three-dimensional image through a computerized tomography (CT scanning) such that the pinhole formed within the unit can be effectively detected.

It is understood that the term "vehicle" or "vehicular" or other similar term as used herein is inclusive of electric motor vehicles in general such as passenger automobiles including sports utility vehicles (SUV), buses, trucks, various commercial vehicles, watercraft including a variety of boats and ships, aircraft, and the like, and includes hydrogen-powered vehicles (e.g. fuels derived from resources hydrogen).

The above features and advantages of the present invention will be apparent from or are set forth in more detail in the accompanying drawings, which are incorporated in and form a part of this specification, and the following Detailed Description, which together serve to explain by way of example the principles of the present invention.

BRIEF DESCRIPTION OF THE DRAWINGS

The above and other features of the present invention will now be described in detail with reference to certain exemplary embodiments thereof illustrated by the accompanying drawings which are given hereinafter by way of illustration only, and thus are not limitative of the present invention, and wherein.

Figure 1:
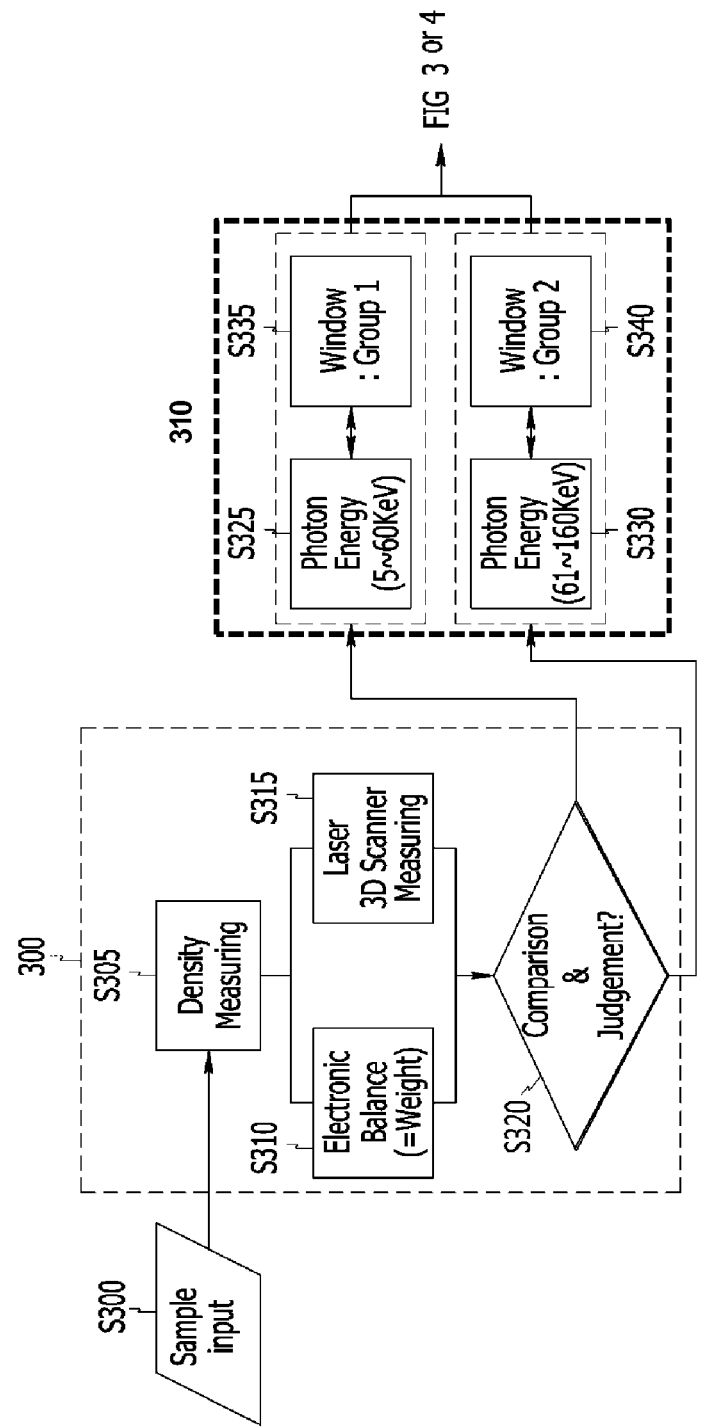
FIG. 1 is a schematic flow diagram showing a density evaluation of a fuel cell element unit and selection of the photon energy level of X-ray and window system according to a density level of a fuel cell element unit.

Reference numerals set forth in the Drawings includes reference to the following elements as further discussed below:

100, 200: X-ray source
110, 240: fuel cell element unit
120, 270: image detector
130, 250: stage
140, 260: drive portion
150, 280: computer tomography
210: filter
220: condense lens
230: zone plate It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

DETAILED DESCRIPTION OF THE EMBODIMENTS

As described herein, the present invention features a pinhole detection system of fuel cell element units, comprising a stage on which density (weight/volume) of a fuel cell element unit is suitably measured by electronic weight balance and 3D Scan type volume integrator to evaluate weight and volume, respectively, photon energy ranges of x-ray beam and window species of the pinhole detection system automatically select according to the density reference point of 2.0 g/cm$^3$ for a fuel cell element unit, a fuel cell element unit is disposed, a drive portion that is configured to move the stage, an X-ray source that applies X-ray to the fuel cell element unit, an image detector that detects X-ray penetrating the fuel cell element unit, and a computer tomography unit.

In one embodiment, the drive portion is configured to move the stage so as to rotate the fuel cell element unit.

In another embodiment, the X-ray source is disposed at one side of the stage to apply X-ray to the fuel cell element unit.

In another further embodiment, the computer tomography unit reconstructs a tomogram that is detected by the image detector to a three dimensional image.

Certain exemplary embodiments of the present invention will hereinafter be described in detail with reference to the accompanying drawings.

FIG. 1 is a schematic flow diagram showing a density evaluation of a fuel cell element unit and selection of the photon energy level of X-ray and window system according to a density level of a fuel cell element unit.

A fuel cell element unit is put as a fuel cell sample in a step S300, and a density measurement and calculation mode is performed to detect a density of the fuel cell element unit in a step S305. The density measurement and calculation mode is performed by a density detection unit 300 shown in FIG. 1.

The density detection unit performs a step S310 and a step S315, the weight of the fuel cell element unit is measured by an electronic weight balance in a step S310, and the volume of the fuel cell element unit is measured by a laser 3D scan type volume integrator in a step S315.

Next, a comparison determination process in a step S320 uses the weight and the volume of the fuel cell element unit, calculates a density of the fuel cell element unit, and determines whether the density is less than or equal to 2.0 g/cm$^3$, or more than 2.0 g/cm$^3$.

FIG. 1 further depicts a determiner 310, where if it is determined that the density of the fuel cell element unit is less than or equal to 2.0 g/cm$^3$, a step S325 and a step S335 of the determiner 310 are performed, and if it is determined that the density of the fuel cell element unit is larger than 2.0 g/cm$^3$, a step S330 and a step S340 of the determiner 310 are performed.

The photon energy that is outputted from an X-ray source can be one value ranging from 5 to 60 KeV in a step S325, and a window group 1 is selected in a step S325. Here, one of the window groups 1 is Be, which has a characteristic that the loss rate of X-ray thereof is low.

Accordingly, the X-ray that is radiated by an X-ray source penetrates the window group 1 to be radiated to the fuel cell element unit.

The photon energy that is outputted by the X-ray source can be one value ranging from 61 to 160 KeV in a step S330, and a window group 2 is selected in a step S340. Here, the window group 2 can include one of boron nitride family, silicon, nitride family, and polymer family.

Accordingly, the X-ray that is radiated from a X-ray source penetrates the window group 2 to be radiated to the fuel cell element unit.

Figure 2:
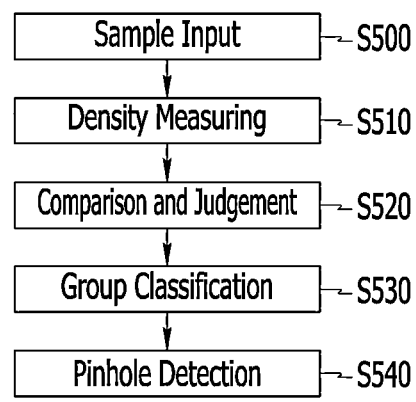
FIG. 2 is a schematic flow chart showing a density evaluation of a fuel cell element unit, selection of the photon energy level of X-ray and window system according to a density level of a fuel cell element unit, and detection of a pinhole for a fuel cell element unit according to an exemplary embodiment of the present invention.

FIG. 2 is a schematic flow chart showing a density evaluation of a fuel cell element unit, selection of the photon energy level of x-ray and window species (or system) according to a density level of a fuel cell element unit, and detection of a pinhole for a fuel cell element unit according to an exemplary embodiment of the present invention.

Referring to FIG. 2, a pinhole detection method includes a S500 step that the fuel cell element unit is put as a sample, a S510 step that measures the density of the fuel cell element unit, and a S520 step that compares the density of the fuel cell element unit with predetermined values so as to judge a photon energy level.

The method includes a S530 step that classify the groups depending on the density and a S540 step that detects a pinhole of the fuel cell element unit depending on the classified group.

Figure 3:
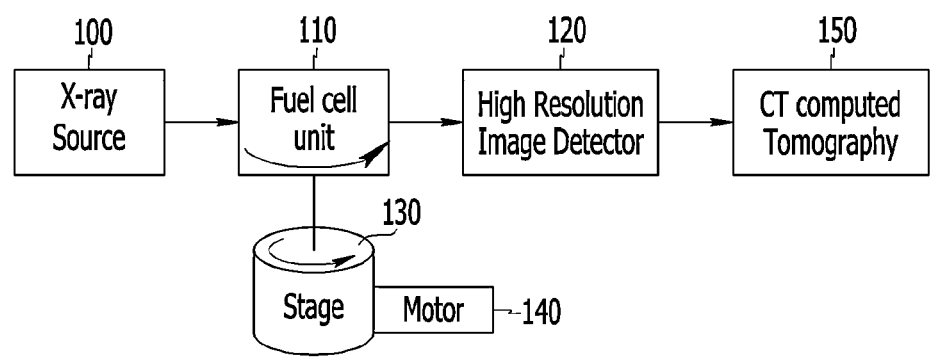
FIG. 3 is a schematic diagram of a pinhole detection section in this invention system of a fuel cell element unit according to an exemplary embodiment of the present invention.
Figure 4:
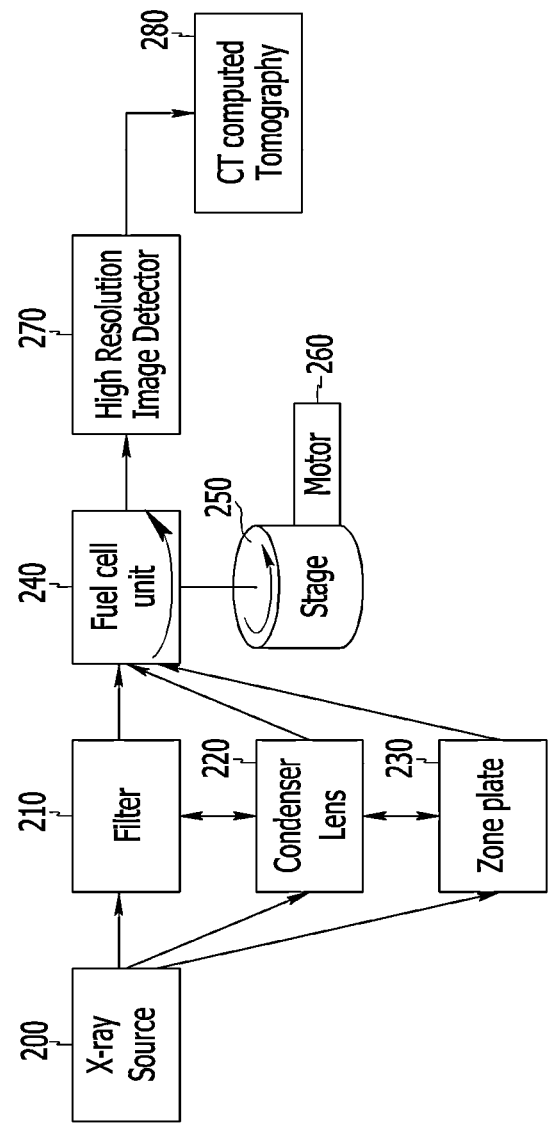
FIG. 4 is a schematic diagram of a pinhole detection section in this invention system of a fuel cell element unit according to another exemplary embodiment of the present invention.

After the density of the fuel cell element unit is measured in the FIG. 1, a process that detects a pinhole of the fuel cell element unit on a stage shown in FIGS. 3 and 4 is performed.

FIG. 3 is a schematic diagram of a pinhole detection system of a fuel cell element unit according to an exemplary embodiment of the present invention.

Referring to FIG. 3, a pinhole detection system of a fuel cell element unit preferably includes an X-ray source 100, a fuel cell element unit 110, a stage 130, a drive portion 140, an image detector 120, and a computer tomography 150 reconstructing a tomogram that is suitably detected by the image detector 120 to a three-dimensional image.

Preferably, the X-ray source 100 has a capacity ranging from 2 to 160 keV, and preferably uses rhodium (Rh), chrome (Cr), copper (Cu), or tungsten (W) as a target.

According to preferred exemplary embodiments, the fuel cell element unit 110 is three layers of membrane-electrode assembly (MEA), five layers of membrane-electrode assembly that two layers of gas diffusion layer (GDL) are hot pressed, and a separating plate (or a bipolar plate).

Preferably, the fuel cell element unit 110 is suitably disposed on the stage 130, and the stage 130 rotates the fuel cell element unit 110 by the drive portion 140 such as a motor.

In certain preferred embodiments, the X-ray source 100 suitably applies X-ray to the fuel cell element unit 110 rotating, and the image detector 120 detects the X-ray penetrating the fuel cell element unit 110. In further preferred embodiments, a plurality of projections that are detected by the image detector 120 are suitably reconstructed in a three-dimensional image by the computer tomography 150 to effectively display a pinhole of the fuel cell element unit 110.

The methods by which the image detector and the computer tomography detect and reconstruct the detected projections to a three-dimensional tomogram are known to one of skill in the art, and thus a detailed description thereof is omitted.

In another exemplary embodiment of the present invention, the MEA and the GDL are suitably joined to form a configuration of five layers, wherein a pinhole can be suitably formed on an electrolyte membrane of the MEA by carbon fiber of the GDL. In further preferred embodiments, while the bipolar plate is suitably pressed to be manufactured, the pinhole can be formed therein.

Preferably, the image detector 120 effectively detects the pinhole that is suitably formed inside the fuel cell element unit 110 to improve productivity.

In another further exemplary embodiment of the present invention, minimum focus of the X-ray source 100 preferably ranges from 0.1 to 10 μm, the capacity thereof preferably ranges from 2 to 160 keV, Rh, Cr, Cu, or W is preferably used as a target, the resolution of the image detector 120 is smaller than 1 μm, and the magnification thereof preferably ranges from 2000 to 15,000.

In other further embodiments, it is desirable that vacuum rate of the light radiation pipe of the X-ray source 100 is lower than $10^{-7}$ torr and that a beryllium window, which is low in absorption rate, is preferably used where the output capacity of the X-ray source 100 is less than or equal to 60 keV such as 2~60 keV.

Preferably, as a pinhole measure object, high molecular electrolyte membrane, catalyst, and carbon paper are suitably prepared, and laser is used to voluntarily form a pinhole of 10 to 15 μm in the electrolyte membrane that is three layer membrane electrode assembly (MEA).

Further, the GDL is hot pressed on both sides of the three layer MEA in which the pinhole is suitably formed, such that five layers MEA is fabricated.

Figure 5:
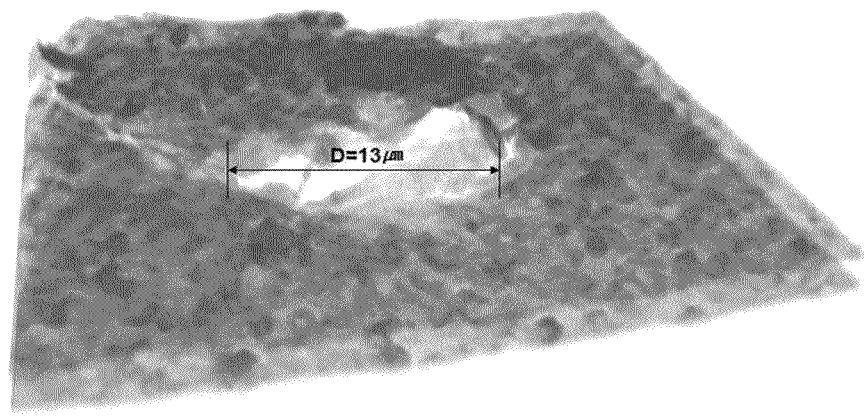
FIG. 5 shows a pinhole detection result according to an exemplary embodiment of the present invention.

In another further embodiment, the pinhole detection system of a fuel cell element unit 110 is used to suitably detect a pinhole of about 13 μm. For example, FIG. 5 shows a pinhole detection result according to another exemplary embodiment of the present invention.

Preferably, the capacity of the X-ray source 100 is 5.4 keV, and Cr is used as a target. Further, depending on an experimental condition or a design specification, the capacity of the X-ray source 100 and a kind of a target can be optionally varied.

FIG. 4 is a schematic diagram of a pinhole detection system of a fuel cell element unit according to another exemplary embodiment of the present invention.

In further exemplary embodiments and referring to FIG. 4, a pinhole detection system of a fuel cell element unit preferably includes a X-ray source 200, a filter 210, a condense lens 220, a zone plate 230, a fuel cell element unit 240, a stage 250, a drive portion 260, an image detector 270, a computer tomography (280, CT: computed tomography).

Preferably, the filter 210 filters a predetermined wavelength from an x-ray that is applied from the X-ray source 200, and the condense lens 220 or the zone plate 230 focuses the x-ray generating in a predetermined area.

As described herein, the fuel cell element unit 240 is suitably disposed on the stage 250, and the stage 250 rotates the fuel cell element unit 240 by the drive portion 260.

Preferably, X-ray that is suitably generated from the X-ray source 200 is applied to the fuel cell element unit 240 rotating by the stage 250, and the image detector 270 detects the X-ray penetrating the fuel cell element unit 240.

In further preferred embodiments, the image detector 270 suitably detects the inner shape of the fuel cell element unit 240 rotating, and a plurality of projections that are detected by the image detector 270 are suitably reconstructed in a three-dimensional image by the computer tomography 280.

Referring to FIGS. 3 and 4, the method for detecting a pinhole of the fuel cell element unit 110, 240 includes a step that puts the fuel cell element unit 110, 240 on the stage 130, 250, a step in which the stage 130, 250 rotates the fuel cell element unit 110, 240, a step that applies a predetermined amount of X-ray from an X-ray source 100, 200 a step that a X-ray that passes a filter 210, a condense lens 220, or a zone plate 230, or a window (group 1 or group 2) passes the fuel cell element unit 110, 240, a step that detects a plurality of projections by a high resolution image detector 120, 270, and a step that reconstructs a three dimensional tomogram by the computer tomography 150, 280 as described above.

Like this, the image that is reproduced to 3D image is analyzed to be able to effectively detect or determine a pinhole of the fuel cell element unit.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A pinhole detection system of a fuel cell element unit, comprising:
 a density detection module that detects a density of a fuel cell element unit;
 a stage on which a fuel cell element unit is disposed to be detected;
 a drive portion that is configured to move the stage so as to rotate the fuel cell element unit;

an X-ray source that is disposed at one side of the stage to apply X-ray to the fuel cell element unit that rotates;

an image detector that detects an X-ray penetrating the fuel cell element unit;

a computer tomography that reconstructs a three dimensional tomogram wherein a plurality of projections that are detected by the image detector are used to form a three dimensional tomogram, and a determiner that selects a photon energy level of an x-ray and a X-ray window according to the density of the fuel cell element unit;

wherein a focus of the X-ray source ranges from 0.1 to 10 μm, a capacity thereof ranges from 2 to 160 keV, a target thereof includes Rh, Cr, Cu, or W, and the X-ray window is made of one of beryllium, boron family, silicon, nitride family, or polymer family, a resolution of the image detector is lower than 1 μm, a magnification thereof ranges from 2000 to 15,000, and a vacuum rate inside a discharge pipe of the X-ray source is below $10^{-7}$ torr.

2. The pinhole detection system of claim 1, further comprising group 1 and group 2 modules with different systems of photon energy level and a window group based on a reference point 2.0 g/cm³ that is a density of a fuel cell element unit.

3. The pinhole detection system of claim 2, wherein if the density of the fuel cell element unit is lower than or equal to a predetermined density value of the 2.0 g/cm³, the determiner selects the group 1 in which an X-ray photon energy level is less than or equal to 60 keV and the X-ray window is made of beryllium, and if the density of the fuel cell element unit is larger than a predetermined density value of the 2.0 g/cm³, the determiner selects the group 2 in which an X-ray photon energy level is in a range of 61~160 keV and the X-ray window is made of one of boron family, silicon, nitride family, or polymer family.

4. The pinhole detection system of claim 1, further comprising a condense lens that is disposed between the X-ray source and the fuel cell element unit, through which X-ray penetrates.

5. The pinhole detection system of claim 1, further comprising a filter that is disposed between the X-ray source and the fuel cell element unit, through which X-ray penetrates.

6. The pinhole detection system of claim 1, further comprising a zone plate that is disposed between the X-ray source and the fuel cell element unit, through which X-ray penetrates.

* * * * *

UNITED STATES PATENT AND TRADEMARK OFFICE
CERTIFICATE OF CORRECTION

PATENT NO. : 9,170,216 B2
APPLICATION NO. : 14/150116
DATED : October 27, 2015
INVENTOR(S) : Sang Yeoul Ahn et al.

Page 1 of 1

It is certified that error appears in the above-identified patent and that said Letters Patent is hereby corrected as shown below:

On the title page of the patent, in column 1, after item (65), insert:

--(63) Related U.S. Application Data

Continuation-in-part of application No. 14/100,900, filed on December 9, 2013, which is a continuation-in-part of application No. 12/815,320, filed on June 14, 2010, now abandoned.--

Signed and Sealed this
Fourteenth Day of June, 2016

Michelle K. Lee
*Director of the United States Patent and Trademark Office*